(12) United States Patent
Erickson

(10) Patent No.: US 7,718,715 B2
(45) Date of Patent: May 18, 2010

(54) PH-MODIFIED LATEX COMPRISING A SYNERGISTIC COMBINATION OF BIOCIDES

(75) Inventor: Anita S. Erickson, Racine, WI (US)

(73) Assignee: S.C. Johnson & Son, Inc., Racine, WI (US)

( * ) Notice: Subject to any disclaimer, the term of this patent is extended or adjusted under 35 U.S.C. 154(b) by 1174 days.

(21) Appl. No.: 10/864,967

(22) Filed: Jun. 10, 2004

(65) Prior Publication Data

US 2005/0277707 A1  Dec. 15, 2005

(51) Int. Cl.
- C09D 5/16 (2006.01)
- A61K 31/275 (2006.01)
- A61K 31/13 (2006.01)
- A01N 37/34 (2006.01)
- A01N 33/24 (2006.01)
- A01N 25/08 (2006.01)
- A01N 33/18 (2006.01)

(52) U.S. Cl. .................. 523/122; 424/409; 514/525; 514/640; 514/727

(58) Field of Classification Search .......... 514/527, 514/727, 640, 526; 523/122; 106/18.32; 424/409

See application file for complete search history.

(56) References Cited

U.S. PATENT DOCUMENTS

| | | | |
|---|---|---|---|
| 3,261,796 A * | 7/1966 | Simms | .......... 524/802 |
| 4,725,587 A | 2/1988 | Whitekettle et al. | |
| 4,725,624 A | 2/1988 | Whitekettle et al. | |
| 4,732,905 A | 3/1988 | Donofrio et al. | |
| 4,732,911 A | 3/1988 | Whitekettle et al. | |
| 4,732,913 A | 3/1988 | Donofrio et al. | |
| 4,753,961 A | 6/1988 | Donofrio et al. | |
| 4,855,296 A | 8/1989 | Donofrio et al. | |
| 4,857,557 A | 8/1989 | Donofrio et al. | |
| 4,859,702 A | 8/1989 | Whitekettle et al. | |
| 4,859,705 A | 8/1989 | Donofrio et al. | |
| 4,859,708 A | 8/1989 | Donofrio et al. | |
| 4,863,960 A | 9/1989 | Donofrio et al. | |
| 4,966,775 A | 10/1990 | Donofrio et al. | |
| 5,045,104 A | 9/1991 | McCoy | |
| 5,196,443 A | 3/1993 | Oppong et al. | |
| 5,439,970 A * | 8/1995 | Reeb | .......... 524/558 |
| 5,444,088 A * | 8/1995 | Syrinek | .......... 514/526 |
| 5,460,797 A | 10/1995 | Ryan | |
| 5,874,476 A * | 2/1999 | Hsu et al. | .......... 514/640 |
| 6,149,927 A | 11/2000 | Ghosh | |
| 6,153,571 A | 11/2000 | Komocki et al. | |
| 6,177,070 B1 | 1/2001 | Lynch | |
| 6,348,483 B1 | 2/2002 | Beilfuss et al. | |
| 6,361,788 B1 | 3/2002 | Antoni-Zimmerman et al. | |
| 2002/0028754 A1 * | 3/2002 | Johansen et al. | .......... 510/302 |
| 2004/0082495 A1 * | 4/2004 | Maleeny et al. | .......... 512/1 |

FOREIGN PATENT DOCUMENTS

WO  WO 01/23510 A2  4/2001
WO  WO 02/089759  * 11/2002

OTHER PUBLICATIONS

Lambert, et al. Journal of Aplied Microbiology, 2003, 94, 747-759.*

* cited by examiner

*Primary Examiner*—Johann R Richter
*Assistant Examiner*—Mei-Ping Chui

(57) ABSTRACT

A stabilized latex with improved antimicrobial features is disclosed. In preferred embodiments, this latex comprises a mixture of 2-bromo-2-nitro-1,3-propanediol and 4,4-dimethyl-oxazolidine or 2-bromo-2-nitro-1,3-propanediol and 1-(3-chloroallyl)-3,5,7-triaza-1-azoniaadamantane chloride.

5 Claims, No Drawings

PH-MODIFIED LATEX COMPRISING A SYNERGISTIC COMBINATION OF BIOCIDES

CROSS-REFERENCE TO RELATED APPLICATION

Not Applicable

STATEMENT REGARDING FEDERALLY SPONSORED RESEARCH OR DEVELOPMENT

Not Applicable

BACKGROUND OF THE INVENTION

This invention relates to stable, aqueous latexes having biocidal properties and to methods for their preparation. Specifically, the present invention provides a combination of biocides to provide antimicrobial protection that individual biocides cannot provide. The combination is especially suitable where latexes have been pH adjusted into a pH range that provides thermostability but provides a more susceptible environment for microbial attack.

Aqueous dispersions of polymers, which are referred to as "latexes" in the art, are generally known to be useful, both alone and in a variety of coatings, including films, polishes, varnishes, paints, inks, and adhesives. A wide variety of latexes of various homopolymeric and copolymeric compositions (such as styrene-butadiene copolymers, acrylic homopolymers and copolymers, vinylidene chloride homopolymers and copolymers, etc.) have been developed having specific chemical and/or mechanical properties for particular end use applications.

For example, the stabilized latex emulsion described in U.S. Pat. Nos. 5,081,166 and 4,894,397 is a stabilized latex emulsion produced by: (i) reacting latex-forming monomers under emulsion-polymerization reaction conditions to form a hydrophilic first-stage polymeric precursor; (ii) contacting the first-stage polymeric precursor with at least one hydrophobic latex-forming monomer under emulsion-polymerization reaction conditions to form a hydrophobic second-stage polymeric precursor such that a portion of the second-stage hydrophobic polymeric precursor partitions into the first-stage hydrophilic polymeric precursor thereby producing an inverted core-shell latex emulsion polymeric precursor; and (iii) adjusting the pH of the inverted core-shell latex emulsion polymeric precursor to dissolve at least a portion of the first stage hydrophilic polymeric precursor thereby producing a stabilized latex emulsion including a continuous aqueous phase containing the first-stage hydrophilic polymeric precursor and a discontinuous phase containing discrete, stabilized particles of the second-state hydrophobic polymeric precursor. The resulting stabilized emulsion can be used to produce a variety of coatings including films, polishes, varnishes, paints, inks, and adhesives.

In the process of U.S. Pat. Nos. 5,081,166 and 4,894,397, the step of adjusting the pH of the inverted core-shell latex emulsion for dissolving the hydrophilic polymer is particularly advantageous as it serves to produce a stabilized latex emulsion. If acidic functional group monomers are selected for the first-stage polymer used in producing the inverted core-shell latex, addition of a suitable base is appropriate for adjusting the pH of the inverted core-shell latex emulsion toward or to a neutral pH.

It has been discovered, however, that raising the pH has drawbacks in certain applications of latexes. Specifically, raising the pH has the effect of reducing the number of acid groups which are known to have bactericidal or bacteriostatic properties. In environments where the latex is prone to bacterial growth, the elimination of acid groups may lead to bacterial growth in the latex.

Therefore, it would be beneficial to provide a latex having the dual advantages of stabilization through pH adjustment and bactericidal or bacteriostatic properties.

BRIEF SUMMARY OF THE INVENTION

In one embodiment, the present invention is a pH stabilized latex, comprising a mixture of 2-bromo-2-nitro-1,3-propanediol and 4,4-dimethyl-oxazolidine, wherein the mixture provides synergistic biocidal activity, particularly synergistic anti-fungal activity. Preferably, the latex is an acrylic latex and the latex comprises acid functional monomers.

In another embodiment, the present invention is the latex described above, wherein 2-bromo-2-nitro-1,3-propanediol is between 0.12% (360 ppm active ingredient) and 0.16% (480 ppm active ingredient) of the latex and wherein 4,4-dimethyl-oxazolidine is between 0.3% and 0.5% of the latex.

In another embodiment, the latex is incorporated in a product selected from the group consisting of coatings, films, polishes, varnishes, paints, inks, adhesives and in floor finishes.

In another embodiment, the present invention is a pH stabilized latex comprising a mixture of 1-(3-chloroallyl)-3,5,7-triaza-1-azoniaadamantane chloride and 2-bromo-2-nitro-1,3-propanediol, wherein the mixture provides synergistic biocidal activity.

Preferably, the latex is an acrylic latex and comprises acid functional monomers.

In another embodiment, 2-bromo-2-nitro-1,3-propanediol is between 0.12% (360 ppm active ingredient) and 0.16% (480 ppm active ingredient) of the latex and 1-(3-chloroallyl)-3,5,7-triaza-1-azoniaadamantane chloride is between 0.3% and 0.5% of the latex.

In another embodiment, this latex is incorporated in product selected from the group consisting of coatings, films, polishes, varnishes, paints, inks, adhesives and floor finishes.

In another embodiment, the invention is a method of stabilizing a latex comprising the steps of creating a pH stabilized latex with the addition of a mixture of 2-bromo-2-nitro-1,3-propanediol and 4,4-dimethyl-oxazolidine, wherein the mixture provides synergistic biocidal activity or a mixture of 1-(3-chloroallyl)-3,5,7-triaza-1-azoniaadamantane chloride and 2-bromo-2-nitro-1,3-propanediol wherein the mixture provides synergistic biocidal activity.

Other objects, features or embodiments of the present invention will be apparent to one of skill in the art after examination of the specification, claims and drawings.

DETAILED DESCRIPTION OF THE INVENTION

In General

Latexes are typically used as a component in many commercial and industrial products, such as coatings, films, polishes, varnishes, paints, inks, adhesives and floor finishes. In many instances, these latexes do not require further antimicrobial or preservative additions. For example, many of these acrylic latexes, such as acrylic latex A (described below), may have a pH between 2-3 and need no preservative.

However, these latexes are not stable to hot or cold temperature. One typical way to stabilize latexes is by partial or optimal neutralization with ammonia. When we refer to a "stabilized acrylic latex" we mean to encompass an acrylic latex that has been pH adjusted so that the latex is stable. In the Examples below the pH was adjusted to pH 6-7.

However, once one has neutralized the latex, one must address the need for antimicrobial or biocidal additives. (By the terms "antimicrobial" and "biocidal" we mean to include anti-fungal, anti-yeast and anti-bacterial properties.) Our challenge test results initially showed that the maximum allowable level for BRONOPOL (2-bromo-2-nitro-1,3-propanediol, BNPD) failed to control the growth of *Aspergillus niger* and the maximum allowable level for BIOBAN CS-1135 (4,4-dimethyl-oxazolidine) failed to control *Candida albicans* in a test stabilized acrylic latex. Similarly, the maximum allowable level for DOWICIL 75 (1-(3-chloroallyl)-3,5,7-triaza-1-azoniaadamantane chloride) failed to control *Candida albicans* in the test stabilized acrylic latex.

Surprisingly, we found that a combination of BRONOPOL and BIOBAN CS-1135 and a combination of BRONOPOL and DOWICIL 75 provided synergistic fungal enhancement of biocidal activity. Therefore, a fully stabilized latex would comprise both pH modification and a synergistic combination of biocides.

In one embodiment, the present invention is a combination of BRONOPOL and BIOBAN CS-1135 in a stabilized latex, preferably an acrylic latex. The Examples below disclose that the combination of 0.16% BRONOPOL and 0.5% BIOBAN CS-1135 showed the synergistic result of killing both *Aspergillus niger* and *Candida albicans* in the test stabilized acrylic latex A. In another version, the present invention is a combination of BRONOPOL and DOWICIL 75 in a stabilized latex, preferably an acrylic latex. The combination of 0.16% BRONOPOL and 0.15% DOWICIL 75 also gave a similar synergistic result in the stabilized latex A. These two combinations were also found to work effectively in controlling the fungal growth in another test latex described below (acrylic latex B).

Suitable Latexes

We envision that the present invention would be suitable for a wide variety of latexes. Latex generated by polymerization of acrylic esters would be especially preferred for the present invention. For example, acrylic monomers suitable for latexes of the present invention would include ethyl, butyl and 2-ethylhexyl acrylate, as well as methyl and butyl methacrylate. Styrene is typically copolymerized with these acrylic monomers, although other copolymerizations may be used.

The examples in this case represent state of the art surfactant-supported acrylic latexes made by the semicontinuous batch process where the monomers are added at a controlled rate so the reaction exotherm can be controlled. In addition, they have an acid functional monomer, MAA (methacrylic acid), incorporated into the polymer backbone, which can provide additional ionic stabilization when partially or totally neutralized with a base to form a carboxyl salt. In some cases, although not used with these examples, the semi-continuous process involves a precharge of a small amount of the monomer into the reactor to form a seed latex prior to the addition of the remainder of the monomers. The number of latex particles in the seed is a tool to help control the final particle size of the finished batch.

The first latex (latex A) also represents a latex that can go from the colloidal dispersion form when not neutralized to a water-soluble polymer when fully neutralized. This solubility is accomplished by the proper level of acid functionality and the use of a chain transfer agent (IOMPA) to lower the molecular weight. This latex was made without any base (such as ammonia) and it has a pH<3. At this pH, it is in the colloidal form, but it is not stable to freeze-thaw or elevated temperatures. It will also gel at extended times (about 1 year) at room temperature. However, it is relatively resistant to microbes when it is at an acidic pH. This latex can be stabilized to hot and freezing temperatures, and remain in colloidal form, by partial neutralization of the acid. However, this brings the pH into the 6-7 pH range and the latex is much more susceptible to microbial attack. This latex cannot be fully neutralized (at the weight solids at which it was made) or it will go into solution and the viscosity will be too high to be useful.

The second latex (latex B) will not go into solution when all the acid is neutralized because the acid functionality is lower and the molecular weight is very high since a chain transfer agent was not used. Ammonia is added at the end of the reaction to provide carboxyl groups to help stabilize the latex. Its pH is also in the near neutral range and susceptible to microbial attack. This latex was also well protected by the combination of biocides.

Other types of "state of the art" latices or latexes are made by varying the rates and composition of monomer addition. For example, "core-shell" latexes are made by adding a blend of monomers from the first monomer tank to the reactor. These form the core or the latex particles. A second, and different blend, of monomers is then fed into the reactor to form the shell of the latex particles. A variation of this process called a "linear power feed," simultaneously feeds a second tank of well-mixed monomers into the first tank of well-mixed monomers as the first tank is being fed into the reactor. This results in a continuous change from the composition of the first tank to the composition of the second tank during the polymerization process.

Resin supported latexes, such as exemplified in U.S. Pat. Nos. 4,839,413 and 5,216,064 and U.S. application 2004/0044124 A1, are also suitable latexes for the present invention.

We emphasized acrylic latexes, but the biocidal protection is expected to be effective with other types of latices or latexes, such as ethylene-vinyl acetate, vinyl acetate (and other vinyl esters), styrene butadiene, polyurethane dispersions and vinylidene chloride-acrylate. We expect the protection to be effective with other types of latexes as long as the biocides are stable at the desired pH.

Suitable Preparation Steps

The Examples below describe one typical way of incorporating the biocides into the stabilized acrylic latex. Other ways of incorporating the biocides would be apparent to one of skill in the art. The biocide is typically added at the completion of the emulsion procedure.

Suitable Biocides

The present invention involves the incorporation of BRONOPOL, BIOBAN CS-1135 and DOWICIL 75 in stabilized acrylic latexes. These biocides can be purchased commercially, typically from The Dow Chemical Company, Midland, Mich.; BASF Biocides Limited, Mount Olive, N.J.; and Avecia Biocides, Wilmington, Del.

The Examples below disclose that a combination of 0.16% BRONOPOL (30% active) and 0.5% BIOBAN CS-1135 is effective and a combination of 0.16% BRONOPOL (30% active) and 0.15 DOWICIL 75 is effective. We believe that the following range of biocide concentration would be suitable for the present invention: One would use between 0.12% and 0.16% BRONOPOL (30% active) and between 0.3% and 0.5% BIOBAN CS-1135 or 0.12% and 0.16% BRONOPOL (30% active) and 0.15% to 0.3% DOWICIL 75.

EXAMPLES

Introduction

Test acrylic latex A (defined below) has a pH between 2-3 and needs no preservative. However, the latex is not stable to hot or cold temperature. One way to stabilize acrylic latex A is by raising the pH with ammonia into the "DN" range of 12-34. (DN is "Degree of Neutralization," or the % of acid groups neutralized by ammonia, and is a preferred calculation of the number of moles of acid that are reacted with ammonia). Having a more neutral pH, addition of preservative is needed to prevent microbial contamination in the stabilized acrylic latex A.

To screen for effective preservatives, the desired preservative is required to pass the Antimicrobial Effectiveness Test or Challenge Test in the laboratory. We describe below the results to testing combinations of BRONOPOL, BIOBAN CS-1135 and DOWICIL 75 with test polymers in our laboratory.

Materials and Methods

Microorganisms

The following cultures were obtained from American Type Culture Collection (ATCC) at 10801 University Boulevard, Manassas, Va. 20110-2209: *Escherichia coli* #11229, *Pseudomonas aeruginosa* #15442, *Candida albicans* #10231, *Aspergillus niger* #6275.

Inocula Preparation

The bacterial inoculum was 0.10 ml of a 1:1 mixture of the 24-hr±4 hr culture of *E. coli* and *P. aeruginosa* in 25 grams of sample to give approximately $4 \times 10^6$ CFU/g. Both *E. coli* culture and the *P. aeruginosa* culture were grown in Nutrient Broth (Difco Laboratories, Detroit, Mich.) at 35° C.

The yeast inoculum was 0.10 ml of a 72-hr±4 hr culture of *C. albicans* in 25 grams of sample to give approximately $2 \times 10^5$ CFU/g. The *C. albicans* culture was grown in Potato Dextrose Broth (Difco Laboratories, Detroit, Mich.) at 28° C.

The mold inoculum was 0.10 ml of *A. niger* culture specimen in 25 grams of sample to give approximately $2 \times 10^5$ CFU/g. The culture specimen was obtained from 7-day-old *A. niger* culture grown on Sabouraud Dextrose Agar (Difco Laboratories, Detroit, Mich.) with 0.2% Triton X-100 in 0.85% saline.

Challenge Test Method

Each of the 25-g samples were inoculated or challenged with 0.10 ml of the bacterial inoculum, the yeast inoculum, and the mold inoculum respectively on day-0 and day-14. All samples were stored at ambient temperature. Each sample (10 microliter) was streaked on appropriate agar plates (bacteria on Tryptic Soy Agar (Difco Laboratories, Detroit, Mich.) plates with neutralizer and yeast/mold on Potato Dextrose Agar (Difco Laboratories, Detroit, Mich.) plates with neutralizer) on day-1, day-2, day-3, day-7, day-14, day-15, day-16, day-17, day-21, and day-28 to test for survivors. Streaked plates were incubated at appropriate temperature and time (48-hr at 35±2° C. for bacteria and 72-hr at 28±2° C. for yeast/mold). On day-14, each sample was re-inoculated with appropriate inoculum after streaking on agar plates. Plates were read after incubation time. Recovery of surviving organisms at 14 days was a failing result for the challenge test.

Polymer Emulsions

We performed our experiments on test samples of acrylic latex. The two sample acrylic latexes we used are described below.

ACRYLIC LATEX A

| Ingredient Name | Percentage |
|---|---|
| Deionized Water | 67.777000 |
| Methyl Methacrylate | 22.729000 |
| Methacrylic Acid 250 PPM MEHQ | 5.682000 |
| Abex JKB (ether sulfate, anionic surfactant, Rhone-Poulenc, Cranberry, NJ) | 2.870000 |
| Isooctyl Mercaptopropionate | 0.371000 |
| Disulfonated Anionic Surfactant | 0.317000 |
| Ammonium Persulfate | 0.284000 |
| Total Percent: | 100.000000 |

ACRYLIC LATEX B

| Ingredient Name | Percentage |
|---|---|
| Deionized Water | 64.294000 |
| Methyl Methacrylate | 11.270000 |
| Butyl Acrylate, 20 PPM MEHQ Inhibited | 9.660000 |
| Styrene, 10-15 PPM P-5-Butyl Catechol | 8.050000 |
| Methacrylic Acid 250 PPM MEHQ | 3.220000 |
| Abex JKB (ether sulfate, anionic surfactant, Rhone-Poulenc, Cranberry, NJ) | 2.150000 |
| GEMTEX 691-40 (anionic surfactant, Fentex, NJ) | 0.805000 |
| Ammonia 20% 21 Degrees BE | 0.251000 |
| Deionized water | 0.150000 |
| Ammonium Persulfate | 0.150000 |
| Total Percent: | 100.000000 |

Both acrylic latex A and acrylic latex B are made by the semi-continuous batch process, where the surfactants and initiator are precharged to the reactor and held at a specified time and temperature, and then the monomers are fed into the reactor by a controlled addition rate.

The following process instructions were followed for acrylic latex A:

DI water (deionized water) is charged into the semicontinuous batch process production reactor (minus about 3% for flushes, etc.) and heated to 79-81° C. The reactor is a standard reactor used to make latex polymers comprising a stirrer and various feed tanks.

Methyl methacrylate (MMA), methacrylic acid (MAA), and isooctyl mercaptopropionate (IOMPA) are charged into the monomer tank and blended thoroughly. Note monomer temperature should be between 4 and 21° C.; the material must be cooled or warmed accordingly.

The surfactants (Abex JKB and disulfonated anionic surfactant) are charged into the reactor.

The reactor is purged with 100% nitrogen for 3 minutes and then reduced to a 20% rate for the remainder of the run.

The ammonium persulfate (APS) is charged into the reactor and the reactor is sealed. Note: monomer addition must begin within 10 minutes of the APS addition.

Monomer charge is begun at a steady rate so that all the monomer is added in 50 minutes.

After monomer addition has been completed, the batch is held at 80° C. for 30 minutes and then cooled to 30-40° C. The batch is then filtered.

The following process instructions were followed for acrylic latex B:

DI water is charged (minus about 3% for flushes, etc.). The surfactants (Abex JKB and Gemtex 691/40) are then charged into the reactor. The reactor is purged with 100% nitrogen and agitation is begun. The reactor is heated to 79-81° C.

Methyl methacrylate (MMA), methacrylic acid (MMA), styrene (STY), and butyl acrylate (BA) are charged into the monomer tank and agitation is begun. Note that monomer temperature should be between 5 and 22° C.; cool or warm accordingly.

Into a small tank, the ammonium persulfate (APS) is charged along with 0.6% of the Di water and mixed. This is charged into the reactor, which is at 80° C. The reactor is sealed.

Agitated for 2-3 minutes (no more than 10 minutes).

The monomer charge is begun at a steady rate so that all the monomer is added in 60 minutes while holding the temperature at 80° C.

After monomer addition has been completed, the batch is heated to 85° C. in the reactor and held 60 minutes to react all the monomers.

Cooled to 45° C. and slowly added a 5:1 mixture of DI water:ammonia (20%) with vigorous agitation.

Cooled to 30-40° C. and then batch is filtered.

The biocides were added to the polymers in the following way:

Biocides were always added after the reaction has been completed and after the batch has been cooled to <50° C. The desired temperature was dependent on the specific biocide. Many biocides become deactivated if exposed to high temperatures for an extended time. Each biocide was diluted with about 5× its weight with DI water and slowly added to the batch with good agitation. The dilution is to prevent the biocide from shocking the latex. The batch was mixed for a minimum of 20 minutes after the biocide was added to ensure good incorporation. If any temporary destabilization to the latex had occurred, it had time to recover prior to filtration.

The biocide is generally added last, after the pH adjustment, so that the biocide does not have to go through a pH change.

Results and Discussion

Challenge Test

The Challenge Test is a qualitative laboratory procedure used to differentiate poorly and marginally preserved products from well-preserved products. Products are intentionally inoculated with test organisms and then evaluated by use of streak plating technique to determine if microbial reduction has been attained.

Challenge test results from Table 1 showed that 2.0% Bioban CS-1135 was required to kill all organisms in the stabilized acrylic latex A and BRONOPOL at 0.5% was required to kill all organisms in the stabilized acrylic latex A. We are interested in lowering the concentration of BRONOPOL and BIOBAN CS-1135 due to regulatory concerns. The highest recommended concentration for BIOBAN CS-1135 is 5000 ppm (0.5%) and the maximum level for BRONOPOL is 500 ppm as an active ingredient. BRONOPOL (Bioban BP-30) used in the study is 30% active. Therefore the highest concentration for the 30% active BRONOPOL is 0.16% (500 ppm as active ingredient).

Results from Table 1 showed that BIOBAN CS-1135 at 1.2% failed to kill yeast (*C. albicans*) and 0.2% BRONOPOL failed to kill the mold (*A. niger*) in acrylic latex A. However, the combination of 0.5% BIOBAN CS-1135 and 0.16% BRONOPOL showed surprising synergistic results of killing both the yeast (*C. albicans*) and the mold (*A. niger*).

Results from Table 3 showed that 0.4% DOWICIL 75 failed to kill the yeast (*C. albicans*) in the stabilized acrylic latex A with DN at 17%. The highest concentration for DOWICIL 75 allowed by US EPA is 0.3%. Surprising synergistic results of killing both the yeast (*C. albicans*) and the mold (*A. niger*) in polymer acrylic latex A were observed with the combination of DOWICIL 75 (0.15%/0.3%) and 0.16% BRONOPOL.

The combination of BIOBAN CS-1135 was found to control the fungal growth in another test latex, acrylic latex B. The same result was found with the combination of DOWICIL 75 and BRONOPOL in acrylic latex B. (Tables 2 and 4)

TABLE 1

Challenge Test Results of Bioban CS-1135 & Bronopol (30% Active) in Stabilized Acrylic Latex A

| Compound A (Bioban CS-1135) | Compound B (Bronopol) | Yeast C. Albicans | Mold A. niger | Bacteria E. coli & P. aeruginosa | Degree of Neutralization | PH |
|---|---|---|---|---|---|---|
| 0.10% | 0.00% | Fail | Fail | Pass | 22% | 6.68 |
| 0.20% | 0.00% | Fail | Pass | Pass | 22% | 6.69 |
| 0.80% | 0.00% | Fail | Pass | Pass | 22% | 6.62 |
| 1.20% | 0.00% | Fail | Pass | Pass | 22% | 6.64 |
| 2.00% | 0.00% | Pass | Pass | Pass | 22% | 6.82 |
| 0.00% | 0.10% | Fail | Fail | Pass | 22% | 6.64 |
| 0.00% | 0.20% | Fail | Fail | Pass | 22% | 6.65 |
| 0.00% | 0.50% | Pass | Pass | Pass | 22% | 6.58 |
| 0.00% | 0.80% | Pass | Pass | Pass | 22% | 6.57 |
| 0.00% | 1.20% | Pass | Pass | Pass | 22% | 6.57 |
| 0.50% | 0.50% | Pass | Pass | Pass | 22% | 6.62 |
| 0.50% | 0.16% | Pass | Pass | Pass | 22% | 6.62 |

TABLE 2

Challenge Test Results of Bioban CS-1135 and Bronopol (30% Active) in Stabilized Acrylic Latex B

| Compound A Bioban CS-1135 | Compound B Bronopol | Yeast C. albicans | Mold A. niger | Bacteria E. coli and P. aeruginosa |
|---|---|---|---|---|
| 0.50% | 0.15% | Pass | Pass | Pass |

TABLE 3

Fungal Challenge Test Results of Dowicil 75 and Bronopol (30% Active) in Stabilized Acrylic Latex A

| Compound A Dowicil 75 | Compound B Bronopol | Yeast C. albicans | Mold A. niger | Bacteria E. coli & P. aeruginosa | Degree of Neutralization | PH |
|---|---|---|---|---|---|---|
| 0.20% | 0.00% | Fail | Pass | Pass | 12% | 6.3 |
| 0.30% | 0.00% | Pass | Pass | Pass | 4% | 5.7 |
| 0.40% | 0.00% | Pass | Pass | Pass | 4% | 5.75 |
| 0.40% | 0.00% | Fail | Pass | Pass | 17% | 6.5 |
| 0.00% | 0.10% | Pass | Fail | Pass | 22% | 6.64 |
| 0.00% | 0.20% | Pass | Fail | Pass | 22% | 6.65 |
| 0.00% | 0.50% | Pass | Pass | Pass | 22% | 6.58 |
| 0.00% | 0.80% | Pass | Pass | Pass | 22% | 6.57 |
| 0.00% | 1.20% | Pass | Pass | Pass | 22% | 6.57 |
| 0.30% | 0.16% | Pass | Pass | Pass | 22% | 6.73 |
| 0.15% | 0.16% | Pass | Pass | Pass | 22% | 6.73 |

TABLE 4

Challenge Test Results of Dowicil 75 and Bronopol (30% Active) in Acrylic Latex B

| Compound A Dowicil 75 | Compound B Bronopol | Yeast C. albicans | Mold A. niger | Bacteria E. coli and P. aeruginosa |
|---|---|---|---|---|
| 0.15% | 0.15% | Pass | Pass | Pass |

Synergy Index

Synergism was determined by the method described by F. C. Kull, P. C. Eisman, H. D. Sylwestrowicz, and R. L. Mayer in Applied Microbiology, Volume 9, pages 538-541, 1961 using the ratio determined by Synergy Index $(SI) = Qa/QA + Qb/QB = 1$ is additivity, $<1$ is synergism, and $>1$ is antagonism where, $Qa$ = concentration of compound A, in the mixture, producing an end point $QA$ = concentration of compound A, acting alone, producing an end point $Qb$ = concentration of compound B, in the mixture, producing an end point $QB$ = concentration of compound B, acting alone, producing an end point According to Kull's synergy method, synergy index $<1$ means synergism has occurred. Table 5 shows that the 0.5% Bioban CS-1135 and the 0.16% Bronopol combination had the synergy index of 0.57 which meant synergism has occurred. Table 6 showed that the combination of 0.15% Dowicil 75 and 0.16% Bronopol had the synergy index of <0.70, which also meant synergism has occurred.

TABLE 5

Synergy Index of Bioban CS-1135 and Bronopol (30% Active) in Test Stabilized Acrylic Latex A

| Organisms | Compound A end-point in % | Compound B end-point in % | Qa/QA | Qb/QB | Synergy Index |
|---|---|---|---|---|---|
| C. albicans & A. niger | 2 | 0 | | | |
| | 0.5 | 0.16 | 0.25 | 0.32 | 0.57 |
| | 0 | 0.5 | | | |
| | 0 | 0.8 | | | |
| | 0 | 1.2 | | | |

Compound A = Bioban CS-1135 (4,4-dimethyl-oxazolidine)
Compound B = Bronopol (2-bromo-2-nitro-1,3-propanediol, 30% active)

TABLE 6

Synergy Index of Dowicil 75 and Bronopol (30% Active) in Test Stabilized Acrylic Latex A

| Organisms | Compound A end-point in % | Compound B end-point in % | Qa/QA | Qb/QB | Synergy Index |
|---|---|---|---|---|---|
| C. albicans & A. niger | >0.4 | 0 | | | |
| | 0.3 | 0.16 | 0.75 | 0.32 | <1.07 |
| | 0.15 | 0.16 | 0.38 | 0.32 | <0.70 |
| | 0 | 0.5 | | | |

TABLE 6-continued

Synergy Index of Dowicil 75 and Bronopol (30% Active) in Test Stabilized Acrylic Latex A

| Organisms | Compound A end-point in % | Compound B end-point in % | Qa/QA | Qb/QB | Synergy Index |
|---|---|---|---|---|---|
| | 0 | 0.8 | | | |
| | 0 | 1.2 | | | |

Compound A = Dowicil 75 [1-(3-chloroallyl)-3,5,7-triaza-1-azoniaadamantane chloride]
Compound B = Bronopol (2-bromo-2-nitro-1,3-propanediol, 30% active)

I claim:

1. A pH stabilized latex comprising a biocidal component consisting essentially of a mixture of 2-bromo-2-nitro-1,3-propanediol and 4,4-dimethyl-oxazolidine, wherein the mixture provides synergistic biocidal activity against yeast, wherein 2-bromo-2-nitro-1,3-propanediol is present in an amount of between 0.15% and 0.16% of the latex, and wherein 4,4-dimethyl-oxazolidine is present in an amount of 0.5% of the latex.

2. The latex of claim 1, wherein the latex is an acrylic latex.

3. The latex of claim 2 wherein the latex comprises acid functional monomers.

4. The latex of claim 1, wherein the latex is incorporated in a product selected from the group consisting of coatings, films, polishes, varnishes, paints, inks, adhesives and floor finishes.

5. The latex of claim 1, wherein the latex is an acrylic latex comprising acid functional monomers selected from the group consisting of methyl methacrylate, methacrylic acid, and isooctyl mercaptopropionate.

* * * * *